United States Patent [19]

Incho

[11] 4,000,266

[45] * Dec. 28, 1976

[54] SYNERGISTIC COMBINATION OF INSECTICIDES

[75] Inventor: Harry Hobart Incho, Medina, N.Y.

[73] Assignees: FMC Corporation, Philadelphia, Pa.; Sumitomo Chemical Company, Limited, Osaka, Japan; part interest to each

[ * ] Notice: The portion of the term of this patent subsequent to May 5, 1987, has been disclaimed.

[22] Filed: Feb. 12, 1971

[21] Appl. No.: 115,072

Related U.S. Application Data

[63] Continuation of Ser. No. 709,219, Feb. 29, 1968, abandoned.

[52] U.S. Cl. .................................. 424/186; 424/285
[51] Int. Cl.$^2$ ...................... A01N 9/08; A01N 9/28

[58] Field of Search ........................... 424/186, 285

[56] References Cited

FOREIGN PATENTS OR APPLICATIONS 646,399    4/1964    Belgium ........................... 424/306

OTHER PUBLICATIONS

Nature, Feb. 4, 1967, pp. 493–494.

*Primary Examiner*—Stanley J. Friedman

[57] ABSTRACT

Two known insecticides, (1-cyclohexene-1,2-dicarboximido)methyl chrysanthemumate and (5-benzyl-3-furyl)methyl chrysanthemumate, in combination form synergistic insecticidal compositions. Insecticidal data demonstrating this synergistic interaction are reported.

6 Claims, No Drawings

SYNERGISTIC COMBINATION OF INSECTICIDES

This application is a continuation of application Ser. No. 709,219, filed Feb. 29, 1968, and now abandoned.

FIELD OF THE INVENTION

This invention pertains to the field of insecticides, particularly those insecticides useful in areas frequented by warm-blooded animals, including man, e.g. in household, industrial, or livestock applications.

DESCRIPTION OF THE PRIOR ART

Among the most widely used insecticides today are the pyrethrins, the active principle of pyrethrum flowers (Chrysanthemum cinerariaefolium), which have a high order of insecticidal activity and a low mammalian toxicity. The relatively high cost and the uncertain supply of pyrethrins have resulted in the preparation of synthetic insecticides which retain the desirable properties of pyrethrins. Certain synthetic products having a basic structural similarity to pyrethrins in that they are esters of 2,2-dimethyl-3-(2-methylpropenyl)cyclopropanecarboxylic acid (which is also known as chrysanthemumic acid and will be so referred to herein) exhibit insecticidal activity of a signficant order. However, such compounds because of their complex chemical structure tend to be difficult or expensive to prepare. Therefore, it is highly desirable to increase the activity of chrysanthemumate insecticides.

The two components of the synergistic compositions of this invention are each known members of this class of synthetic chrysanthemumate esters. (1-Cyclohexene-1,2-dicarboximido)methyl chrysanthemumate is described in Belgian Pat. No. 646,399 to Sumitomo Chemical Company Ltd., and (5-benzyl-3-furyl)methyl chrysanthemumate is described in an article by M. Elliott et al in Nature, dated Feb. 4, 1967, starting at page 493. Synergistic combinations such as those of the present invention result in higher insecticidal activity for a given amount of synthetic chrysanthemumate and thus make possible control of insects at lower cost. Availability of less expensive insecticides is of major importance in the practical control of insects, particularly insects that are vectors for diseases affecting man and domestic animals.

SUMMARY OF THE INVENTION

This invention pertains to novel synergistic combinations of two known chrysanthemumate insecticides. These combinations show greater insecticidal activity than would be expected from the combined effect of the separate components.

DETAILED DESCRIPTION

Each of the two components of the novel synergistic compositions of this invention is known. The preparation and properties of (5-benzyl-3-furyl)methyl chrysanthemumate are described in an article by M. Elliott et al in Nature, dated Feb. 4, 1967, at page 493, and in Belgian Pat. No. 690,984 to National Research Development Corporation. The preparation and properties of the second component, (1-cyclohexene-1,2-dicarboximido)methyl chrysanthemumate, are described in Belgian Pat. No. 646,399 to Sumitomo Chemical Company Ltd. Over a wide range of relative concentrations, these insecticides in combination showed an unusual enhancement of activity, far greater than their mere additive effect. This enhanced effect, commonly called synergism, is seen in the following specific examples:

Insecticidal activity was evaluated using a standard Peet-Grady chamber as described in the test procedure of the Chemical Specialty Manufacturers Association (Soap and Chemical Specialties, 1966 Blue Book, p. 209). A large number of houseflies (Musca domestica L.) were released into the test chamber and then sprayed with twelve ml. of a solution of the insecticide in an inert fly spray base oil (a highly refined kerosene fraction containing up to about 10% of methylene chloride or tetrachloroethylene). At intervals of 3, 5, and 10 minutes after spraying the dead and moribund flies lying on the chamber floor were counted. After the 10 minute count, the chamber was cleared of insecticide by means of a vacuum pump. The dead and moribund flies were collected and kept in a holding cage for 24 hours after which the mortality count was taken. Thus the mortality count is the percentage of the total number of flies introduced into the chamber that were both immobilized within 10 minutes by the spray and dead at the end of 24 hours. In the tests reported below the number of flies for each single test was greater than 75. Results reported in the following table are averages of at least two replicates run on different days, and show the percent mortality of houseflies after 24 hours as defined above, for each component alone, and in synergistic combination.

SYNERGISTIC INTERACTION OF INSECTICIDAL CHRYSANTHEMUMATES

Component A is (5-benzyl-3-furyl)methyl chrysanthemumate.
Component B is (1-cyclohexene-1,2-dicarboximido)methyl chrysanthemumate.

| Grams/ml of A | B | Ratio A:B | % Mortality of Houseflies |
|---|---|---|---|
| 0.035 | 0 | — | 58 |
| 0 | 0.005 | — | 1 |
| 0.035 | 0.005 | 7:1 | 76 |
| 0.030 | 0 | — | 52 |
| 0 | 0.010 | — | 2 |
| 0.030 | 0.010 | 3:1 | 76 |
| 0.020 | 0 | — | 32 |
| 0 | 0.020 | — | 7 |
| 0.020 | 0.020 | 1:1 | 70 |
| 0.030 | 0 | — | 52 |
| 0.020 | 0 | — | 32 |
| 0 | 0.050 | — | 18 |
| 0.025 | 0.050 | 1:2 | 92 |
| 0.010 | 0 | — | 10 |
| 0 | 0.030 | — | 9 |
| 0.010 | 0.030 | 1:3 | 56 |
| 0.005 | 0 | — | 0 |
| 0 | 0.025 | — | 8 |
| 0.0025 | 0.0125 | 1:5 | 18 |
| 0.005 | 0 | — | 0 |
| 0 | 0.035 | — | 16 |
| 0.005 | 0.035 | 1:7 | 28 |

These results show the marked synergistic interaction of the compositions of the invention. Over a wide range of ratios of components the mortality for the combination is unexpectedly greater than that to be expected from the added effects of the individual components. This result is particularly striking in view of the extremely low concentration of total insecticidal components used in the tests reported above.

The synergistic compositions of this invention may be employed to control a variety of crop pests and household pests. They are not usually applied full strength, but are generally incorporated with the adjuvants and carriers normally employed for facilitating dispersion of active ingredients for insecticidal applications, recognizing the accepted fact that the formulation and mode of application may affect the activity of a material. Striking results are obtained when these compositions are applied as space sprays and aerosol sprays, for example, or are formulated into any of the diluted and extended types of formulations used in insecticidal practice, including dusts, wettable powders, emulsifiable concentrates, solutions, granulars, baits, and the like, for application to foliage, within enclosed areas, to surfaces, and wherever insect control is desired.

These synergistic compositions may be made into liquid concentrates by solution or emulsification in suitable liquids, and into solid concentrates by admixing the active components with talc, clays, and other solid carriers used in the insecticide art. Such concentrates normally contain about 5–80% of the toxic composition, and the rest inert material which includes dispersing agents, emulsifying agents, and wetting agents. For practical application, the concentrates are normally diluted with water or other liquid for liquid sprays, with liquefied propellants for aerosols, or with additional solid carrier for application as a dust or granular formulation. Baits are usually prepared by mixing such concentrates with a suitable insect food, such as mixtures of cornmeal and sugar, and insect attractants may also be present. The concentration of the active ingredients in the diluted formulations, as generally applied for control of insects, is normally in the range of about 0.001% to about 5%. Many variations of spraying and dusting compositions are well known in the art, as are the techniques for formulating and applying these compositions.

Employing the synergistic pesticidal compositions described herein, enhanced control is obtained of both crop and household pests, including insects and acarids against which the individual cyclopropanecarboxylates are themselves effective, when used separately at higher concentrations. This includes flying and crawling pests of the orders Coleoptera (beetles), Hemiptera (true bugs), Homoptera (aphids), Diptera (flies), Orthoptera (roaches), Acarina (mites and ticks), and Lepidoptera (butterflies and moths including their larvae). Because of the low mammalian toxicity of these compositions, they are preferred compositions for use in control of pests in an environment inhabited by man and animals, including control of flies, mosquitoes, ants, roaches, moths, ticks, and the like, as well as in uses such as packaging, food and grain protection, and garden, pet, and livestock uses.

The relative amounts of the two component chrysanthemumates are not critical, in that synergistic interaction has been found over a wide range of ratios. Thus one part of (1-cyclohexene-1,2-dicarboximido)methyl chrysanthemumate, on a weight basis the less active insecticide of the two components, has been found to give a synergistic interaction with twenty parts or even more of (5-benzyl-3-furyl)methyl chrysanthemumate. While small amounts of the more active component can synergize much larger amounts of the less active, such combinations are less practical since they tend to require a greater total weight of combined insecticide to achieve a given mortality rate than a less extreme ratio. From practical considerations, it is preferred to employ the two components in ratios in the range of about 10:1 to 1:10 in the synergistic compositions of this invention. It is clear that the components should be present in synergistic proportions, and that effective amounts of the compositions, to control the particular insect pests in the environment of infestation, should be applied.

It is apparent that many modifications may be made in the formulation and application of the compositions of this invention, without departing from the spirit and scope of the invention, and of the following claims.

I claim:

1. An insecticidal composition comprising as the essential active ingredient a combination, in synergistic proportions, of
   A. (5-benzyl-3-furyl)methyl 2,2-dimethyl-3-(2-methyl-1-propenyl)cyclopropanecarboxylate and
   B. (1-cyclohexene-1,2-dicarboximido)methyl 2,2-dimethyl-3-(2-methyl-1-propenyl)cyclopropanecarboxylate.

2. An insecticidal composition comprising as the essential active ingredient a combination of
   A. (5-benzyl-3-furyl)methyl 2,2-dimethyl-3-(2-methyl-1-propenyl)cyclopropanecarboxylate and
   B. (1-cyclohexene-1,2-dicarboximido)methyl 2,2-dimethyl-3-(2-methyl-1-propenyl)cyclopropanecarboxylate
wherein the ratio A:B is in the range of 10:1 to 1:10.

3. The method of controlling insect pests which comprises applying thereto an insecticidally effective amount of a composition of claim 1.

4. The method of controlling insect pests which comprises applying thereto an insecticidally effective amount of a composition of claim 2.

5. An insecticidal composition comprising as the essential active ingredient, a toxic amount of a mixture of 5-benzyl-3-furylmethyl chrysanthemate and 3,4,5,6-tetrahydrophthalimidomethyl chrysanthemate, in a ratio of between about 1:10 and about 10:1.

6. An insecticidal composition comprising as the essential active ingredient, a toxic amount of a mixture of 5-benzyl-3-furylmethyl dl-cis, trans-chrysanthemate and 3,4,5,6-tetrahydrophthalimidomethyl dl-cis, trans-chrysanthemate, in a ratio of between about 1:10 and about 10:1.

* * * * *